United States Patent [19]

Silver et al.

[11] Patent Number: 4,703,108

[45] Date of Patent: Oct. 27, 1987

[54] BIODEGRADABLE MATRIX AND METHODS FOR PRODUCING SAME

[75] Inventors: Frederick A. Silver, Long Valley; Richard A. Berg, Lambertville; David E. Birk, Somerset; Kevin Weadock, Piscataway; Conrad Whyne, Somerset, all of N.J.

[73] Assignee: University of Medicine & Dentistry of New Jersey, Newark, N.J.

[21] Appl. No.: 843,828

[22] Filed: Mar. 26, 1986

Related U.S. Application Data

[63] Continuation of Ser. No. 593,733, Mar. 27, 1984, abandoned.

[51] Int. Cl.$^4$ ............................ A23J 1/10; C08H 1/06
[52] U.S. Cl. ............................. 530/356; 128/DIG. 8; 424/485; 424/94.64; 514/801; 523/105; 523/111
[58] Field of Search ...................... 260/123.7; 527/207; 524/17, 21; 523/105 M; 424/36, 94, DIG. 14; 514/2, 801; 530/356; 128/DIG. 8; 42/484, 485

[56] References Cited

U.S. PATENT DOCUMENTS

| | | | |
|---|---|---|---|
| 3,098,693 | 7/1963 | Sheehan | 106/122 |
| 3,300,470 | 1/1967 | Young | 530/354 |
| 3,800,792 | 4/1974 | McKnight | 128/156 |
| 3,903,882 | 9/1975 | Augurt | 128/155 |
| 3,955,012 | 5/1976 | Okamura | 427/2 |
| 4,060,081 | 11/1977 | Yannas et al. | 128/156 |
| 4,280,954 | 7/1981 | Yannas | 530/356 |
| 4,350,629 | 9/1982 | Yannas | 530/356 |
| 4,352,883 | 10/1982 | Lim | 435/178 |
| 4,363,758 | 12/1982 | Masuho et al. | 424/85 |
| 4,374,121 | 2/1983 | Cioca | 530/356 |
| 4,399,123 | 8/1983 | Oliver | 424/95 |
| 4,409,332 | 10/1983 | Jefferies et al. | 530/356 |
| 4,412,947 | 11/1983 | Cioca | 106/124 |
| 4,418,691 | 12/1983 | Yannas | 128/156.3 |
| 4,458,678 | 7/1984 | Yannas | 128/155 |

FOREIGN PATENT DOCUMENTS

2734503  2/1979  Fed. Rep. of Germany.

OTHER PUBLICATIONS

Doillen et al., Scanning Election Micropscopy 1985, pp. 897–903.
Silver et al., J. Biomedical Materials Research, vol. 13, 701–715 (1979).
Silver et al., Thrombosis Research, vol. 13, pp. 267–277 (1978).
Weadock et al., Biomat, Med.Dev., Art.Org., 11(4),293–318 (1983–84).
Chem. Abstracts 82:744856, 1975, Ruben et al., J. Clinical Pharmacology, pp. 309–312 (1973).
Chemical and Engineering News, Oct. 4, 1965.

*Primary Examiner*—John Kight
*Assistant Examiner*—Nathan M. Nutter
*Attorney, Agent, or Firm*—Weiser & Stapler

[57] ABSTRACT

There are disclosed processes for preparing biodegradable collagen-based matrices in sponge or sheet form wherein in one embodiment a collagen-based material including a collagen selected from the group consisting of types I, II and II collagens is freeze dried to form a collagen-based sponge which is contacted with a cross-linking agent selected from the group consisting of a carbodiimide or a succinimidyl active ester to form an intermediate collagen-based matrix which is subsequently subjected to conditions of severe dehydration to form the collagen-based matrix in sponge or sheet form. In another embodiment, a collagen-based sponge or sheet is first subjected to conditions of severe dehydration followed by contacting the thus formed intermediate collagen-based matrix with a carbodiimide crosslinking compound to form the collagen-based matrix in sponge or sheet form. In still another embodiment of the present invention the cross-linking agent is admixed with the collagen-based material prior to formation of the collagen-based sponge or sheet followed by processing steps of severe dehydration. In a particularly preferred form of the invention, a carrier compound is incorporated during processing to form a collagen-based matrix in sponge or sheet form impregnated with a carrier compound wherein the carrier compound is selected from the group consisting of types IV and V collagen, fibronectin, laminin, hyaluronate, proteoglycan, epidermal growth factor, platelet derived growth factor, angiogenesis factor, antibictic, antifungal agent, spermacidal agent, enzyme and enzyme inhibitor.

38 Claims, No Drawings

BIODEGRADABLE MATRIX AND METHODS FOR PRODUCING SAME

This application is a continuation, of application Ser. No. 593,733, filed Mar. 27, 1984, now abandoned.

FIELD OF THE INVENTION

This invention relates to a biodegradable matrix, and more particularly to a multifunctional collagen-based matrix and/or carrier system thereof.

BACKGROUND OF THE INVENTION

Delivery of drugs, growth factors, hormones, peptides and glycopeptides to external wounds has classically occurred by direct topical application and application to internal wounds by injection into the blood or by absorption into the blood through the digestive system. Controlled release of these agents has been achieved by encapsulation either in bulk or at a microscopic level using synthetic polymers, such as silicone, and natural polymers, such as gelatin and cellulose. The release rate can be controlled for periods of up to a year by proper choice of the polymeric system used to control the diffusion rate (Langer, R. S. and Peppas, N. A., Biomaterials U.S. Pat. No. 2,201,1981). Natural polymers, such as gelatin and cellulose slowly dissolve in a matter of minutes to hours while silicone remains intact for periods of months to years. Biodegradable polymers offer an advantage for controlled release to internal wounds since only a single surgical procedure is necessary.

Collagen is a biodegradable polymer found in animals and in man. It has been used as a plasma expander, vehicle for drug delivery, vitreous body replacement, hemostatic agent, suture material, corneal replacement, hemodialysis membrane, wound dressing and artificial skin, hernia patch, vessel prosthesis, vaginal contraceptive, and injectable agent for tissue augmentation (Chvapil et al., Int. Review of Connective Tissue Research 6, 1, 1973; Chvapil, in Biology of Collagen edited by A. Viidik and J. Vuust, Academic Press, chapter 22, 1980). In most of these applications, the collagen is reconstituted and crosslinked into an insoluble form.

There is described in Yannas et al, (U.S. Pat. No. 4,060,081), the use of collagen and mucopolysaccarides as synthetic skin. Such material is crosslinked using glutaraldehyde, a bifunctional crosslinking agent, which reacts with free amines. One major drawback to using crosslinked collagen has been the adverse biological effects of free glutaraldehyde, a common agent used to crosslink and insolubilize collagen in many applications. Leaching of glutaraldehyde from crosslinked collagens has been shown to be cytotoxic to cells, specifically fibroblasts (Speer et al., J. Biomedical Materials Research 14,753,1980; Cooke et al., British J. Exp. Path. 64,172,1983). Recent evidence suggests that glutaraldehyde polymers and not monomeric glutaraldehyde form crosslinks between collagen molecules; these crosslinks can then rearrange to release free glutaraldehyde and glutaraldehyde polymers (Cheung, D. T. and Nimni, M. D., Connective Tissue Research 10,187–217,1982).

OBJECTS OF THE PRESENT INVENTION

An object of the present invention is to provide a novel biodegradable matrix.

Another object of the present invention is to provide a novel collagen-based matrix.

Still another object of the present invention is to provide a novel collagen-based matrix in sponge or sheet form.

Yet another object of the present invention is to provide a novel biodegradable matrix impregnated with a carrier compound.

A further object of the present invention is to provide a novel biodegradable collagen-based matrix impregnated with a carrier compound.

Yet still another object of the present invention is to provide a novel biodegradable collagen-based matrix impregnated with a carrier compound in sponge or sheet form.

A still further object of the present invention is to provide a novel biodegradable collagen-based matrix impregnated with a carrier compound and is non-toxic and capable of promoting cell growth.

Yet another object of the present invention is to provide a novel biodegradable collagen-based matrix impregnated with a carrier compound for controlled release of drugs.

Yet still another object of the present invention is to provide a novel biodegradable collagen-based matrix impregnated with a carrier compound for topical application to external wounds.

Another object of the present invention is to provide a novel biodegradable collagen-based matrix impregnated with a carrier compound for application to internal wounds.

SUMMARY OF THE INVENTION

These and other objects of the present invention are achieved in one embodiment by forming a sponge or sheet of a collagen-based material including a collagen selected from the group consisting of types I, II and III collagens which sponge or sheet is contacted with a cross-linking agent selected from the group consisting of a carbodiimide or a succinimidyl active ester to form an intermediate collagen-based matrix which is subsequently subjected to conditions of severe dehydration to form a collagen-based matrix in sponge or sheet form. In another embodiment, the sponge or sheet of the collagen-based material is first subjected to conditions of severe dehydration followed by contacting the thus formed intermediate collagen-based matrix with a carbodiimide crosslinking compound to form the collagen-based matrix in sponge or sheet form. In still another embodiment of the present invention the cross-linking agent is admixed with the collagen-based material prior to formation of the intermediate collagen-based sponge or sheet followed by processing steps of severe dehydration. In a particularly preferred form of the invention, a carrier compound is incorporated during processing to form a collagen-based matrix in sponge or sheet form impregnated with a carrier compound wherein the carrier compound is selected from the group consisting of types IV and V collagen, fibronectin, laminin, hyaluronate, proteoglycan, epidermal growth factor, platelet derived growth factor, angiogenesis factor, antibiotic, antifungal agent, spermacidal agent, enzyme and enzyme inhibitor.

DETAILED DESCRIPTION OF THE INVENTION

The collagen-based carrier systems of the present invention are based on the use as a starting material of a soluble or insoluble collagen selected from the group consisting of types I, II and III collagens and mixtures thereof.

Soluble collagens of the types I, II and III collagen are prepared by limited enzymatic digestion of tissue enriched in such collagen types and are formed into collagen-based solution (i.e. a soluble collagen dissolved in a suitable solvent, such as dilute hydrochloric acid, dilute acetic acid or the like).

Insoluble collagens are derived from the following typical sources: type I collagen; bovine, chicken and fish skin, bovine and chicken tendons and bovine and chicken bones including fetal tissues; type II collagen: bovine articular cartilage, nasal septum, sternal cartilage; and type III collagen; bovine and human aorta and skin.

In one embodiment of the present invention, a collagen-based solution or an insoluble collagen dispersed and swollen in a suitable liquid media (e.g. dilute hydrochloric acid, dilute acetic acid or the like) is subjected to a temperature of between about 0° C. to −100° C. to thereby solidify the collagen-based material. Thereafter, the solidified collagen-based material is subjected to a vacuum of less than about 50 millitorr at a temperature of from about 22° C. to −100° C. to form a collagen-based sponge to be further processed, as hereinafter more clearly described. Generally, a weight ratio of soluble or insoluble collagen to solvent or dispersion agent, respectively, of from 1 to 10,000 or from 1 to 15 is used to form the collagen-based solution or dispersion.

In another embodiment of the present invention such a collagen-based solution on a collagen-based dispersion is dried into sheet form prior to further processing as more fully hereinafter described. Drying is effected at temperatures of from 4° C. to 40° C. for a period of time of from 2 to 48 hours.

In one embodiment of the present invention to form a collagen-based matrix, a collagen-based sponge or sheet is first contacted with a crosslinking agent selected from the group consisting of a carbodiimide or N-hydroxysuccinimide derived active esters (succinmidyl active ester) followed by severe dehydration to form the collagen-based matrix. Examples of the carbodiimide include cyanamide and 1-ethyl-3-(3-dimethylaminopropyl)-carbodiimide hydrochloride. Examples of bifunctional succinimidyl active esters including bifunctional N-hydroxysuccinimide, 3,3$^1$-dithio(sulfosuccinimidyl propionate and bis(sulfosuccinimidyl) suberate. When using a carbodiimide crosslinking agent, the collagen-based sponge or sheet is immersed in a carbodiimide solution at a concentration of from about 0.1 to 10% (W/V) maintained at a temperature of from about 2° to 40° C. and at a pH of between 2 to 11 for a period of time of from about 2 to 96 hours. When using a succinimidyl active ester crosslinking agent, the collagen-based sponge or sheet is immersed in a solution thereof at a concentration of from about 0.1 to about 15.0% (W/V) maintained at a temperature of from about 2° to 40° C. for a period of time of from about 2 to 96 hours. The collagen-based sponge or sheet is placed in a solution containing 0.1 to about 15% (W/V) of N-hydroxysuccinimide and carbodiimide at a pH between 2 to 11 for a period of time between 2 to 96 hours at a temperature of from about 2° C. to 40° C. The thus treated intermediate collagen-based matrix is exhaustively washed to remove excess crosslinking agent.

Severe dehydration of the intermediate collagen-based involves conditions of temperature of from 50° C. to 200° C. at a vacuum of 50 millitorr or less for a period of time of from 2 to 96 hours to thereby form the collagen-based matrix. Prior to severe dehydration, the intermediate collagen-based matrix in sponge form is preferably solidified at a temperature of between about 0° C. to −100° C. and thereafter subjected to a vacuum of at least 50 millitorr at a temperature of between about 22° C. and −100° C.

In another embodiment of the present invention to form the collagen-based matrix when using a carbodiimide crosslinking agent, severe dehydration may be effected to form an intermediate collagen-based matrix prior to contracting such an intermediate collagen-based matrix with such a crosslinking agent.

In another embodiment of the present invention to form the collagen-based matrix, the cross-linking agent is premixed with the collagen-based material prior to drying or initiating of freeze drying processing steps.

The collagen-based matrix prepared in accordance with the present invention may be described as a "coral-like" or "scaffold" structure having interstices of a pore size of from 3 to 100 μm., and of a molecular weight of from $10 \times 10^6$ to in excess of $50 \times 10^6$ with a molecular weight between crosslinks from 1,000 to 100,000 via the formation of covalent bonds.

Another embodiment of the present invention is the incorporation of a carrier compound into the collagen-based matrix. Such a carrier compound is selected from the group consisting of collagen types IV and V, fibronectin, laminin, hyaluronate, proteoglycans, epidermal growth factor, platelet derived growth factor, angiogenesis factor, antibiotic, antifungal agent, spermacidal agent, hormone, enzyme and enzyme inhibitor.

Generally, the carrier compound may be introduced at any time during processing of the collagen-based material to the collagen-based matrix in sponge or sheet form. Preferably, a carrier compound is incorporated prior to solidifying of the soluble or insoluble collagen in forming the intermediate collagen-based matrix, or prior to solidifying of the intermediate collagen-based matrix prior to severe dehydration. The carrier materials are added in an amount of from 1 to 30% (w/w) based on the weight of soluble or insoluble collagen. Generally, connective tissue factors, such as fibronectin, types IV and V collagens; laminin, glycosaminoglycans and hyaluronate are incorporated during initial processing steps in forming the collagen-based sponge, or after crosslinking of the intermediate collagen-based matrix. It is preferable to incorporate fibronectin and hyaluronate during forming of the intermediate collagen-based matrix.

There are many sources for the diverse carrier compounds for incorporation into the collagen-based matrix constituting one embodiment of the present invention. Type IV and V collagens are found associated with basement membranes and smooth muscle cells in tissues, respectively. Typical sources of Type IV include the EHS mouse sarcoma tumor, bovine and human placenta, lens capsule and kidney; sources of Type V collagen include placental membranes, ocular tissues and fetal skin (see for example, Trelstad, In Immunochemistry of the Extracellular Matrix, Vol. 1 edited by H. Furthmayr, CRC Press, chapter 2, 1982).

Typical sources of proteoglycans include bovine and human cartilage and synovial fluid, nasal septum and sternal cartilage, and skin. Typical sources for glycoproteins include EHS tumor, bovine and human kidneys, cartilage, bone and placenta as well as bovine and human blood. Typical sources of hyaluronate include rooster comb and bovine vitreous.

Preferred carrier compounds for the collagen-based matrix include fibronectin, laminin, type IV collagen and complexes of hyaluronate and proteoglycans. A value of the swelling ratio of between 2.5 to 5 is required for a collagen-based matrix which comes into contact with open wounds, while a swelling ratio of between 2.5 to 10 are useful for a collagen-based matrix including carrier compounds for subcutaneous implantation. The swelling ratio is defined as the volume of water absorbed per unit volume of collagen-based matrix.

In the case of internal wounds and short-term drug release, collagen-based matrix including a carrier compound in the form of a sheet or a tube is placed in direct contact with tissue.

The biodegradation rate and the release rate can be controlled by variation of the crosslink density. For applications where long term release is desired, a nonporous diffusion layer of a biodegradable polymer, such as poly-3-(hydroxybutyrate) is applied to each side of the collagen-based matrix. For materials to be used on full thickness wounds, a diffusion control layer, such as described in the aforementioned U.S. Letters Patent to Yannas, is applied to prevent diffusion of water or other small volatile molecules from the collagen-based matrix; the diffusion control layer must adhere tightly to the collagen-based matrix layer. The combination of collagen-based matrix layer and diffusion control layer must be strong enough to be sutured and have a tensile strength of at least 100 psi and be able to deform at least 10% before failing. Synthetic non-biodegradable polymers, such as silicone polymers (Silastic Medical Grade Adhesive) or biodegradable polymers, such as polylactic acid, polyglycolic acid, poly-3-(hydroxybutyrate) and copolymers of these materials can be used as the diffusion control layer.

Silicone polymers are preferred materials to control the rate of diffusion of small molecules. Curing of the adhesive in the diffusion control layer can occur without wetting the carrier compound in the collagen-based matrix by dessication at room temperature. A film 0.5 to 1.5 mm in thickness is applied to the matrix layer and is allowed to cure at room temperature for at least 2 hours using a vacuum of 14 in. of Hg.

The thickness of the collagen-based matrix can be varied from 1 to several hundred mm. For full thickness wounds, a thickness of 2 to 3 mm. is desired and enables close contract between the carrier compound in the collagen-based matrix and the wound bed.

When implanted subcutaneously or directly on full thickness dermal wounds, any collagen-based matrix of the present invention does not stimulate the inflammatory process. In addition, chronic implantation results in fibroblast and endothelial cell migration into the collagen-based matrix. The degradation and resorption rate of collagen-based matrices are as assayed in vitro by determination of the time that 1 mg. of the material resists solubilization by 100 units of bacterial collagenase. One unit of collagenase liberates amino acids in collagen equivalent to 1.0 micro mole of L-leucine in 5 hours at 37° C. A combination of succinimidyl active ester formation and severe dehydration or carbodiimide treatment and severe dehydration increases the collagenase resistance time significantly over that observed by any of the procedures heretofore used. These studies indicate that the crosslinking methods of the present invention result in resistance to collagenase degradation and show no stimulation of inflammation.

EXAMPLES OF THE INVENTION

The following examples are illustrative of conditions for the process of the present invention and it is to be understood that the scope of the invention is not be be limited thereby.

EXAMPLE 1

Preparation of Soluble and Insoluble Collagens

The collagen used is prepared from calf hides after the grain layer is separated from the corium or dermis. The corium is cut into pieces, washed, swollen, freeze dried and stored at −20° C.

Soluble collagen is obtained by placing 250 gr. of the freeze dried insoluble collagen in 1.5 liters of HCl at a pH of 2.5 containing 1.5 gr. of crystalline pepsin (Sigma Chemical Company). The mixture is stirred overnight at 4° C. and then filtered through cheese cloth, Whatman filter paper #4 followed by Whatman #42, Gelman 5 $\mu$m and 1.2 $\mu$m filters and finally through Millipore 0.65 $\mu$m and 0.45 $\mu$m filters. The soluble fraction obtained after sequential filtration contains types I, III and V collagens. The soluble collagen fraction is dialyzed against a 1.0M NaCl solution containing 50 mM Tris adjusted to pH 7.5 and enough solid NaCl is added to raise the molarity of the solution to 1.7. The precipitate at 1.7M NaCl is type III collagen and is collected by centrifugation at 10,000×g for 60 minutes and then dialyzed versus 0.005M acetic acid, freeze dried and stored at −20° C. To the supernatant is added additional NaCl to raise the molarity to 2.5M and the precipitate (type I collagen) is pelleted by centrifugation, dialyzed versus 0.005M acetic acid, freeze dried and stored at −20° C. The remaining supernatant contains type V collagen and is dialyzed against 0.005M acetic acid, freeze dried and stored at −20° C.

Insoluble collagen solutions are obtained by dispersing freeze dried corium ground using a Wiley Mill in HCl at pH of 2.5. The swollen collagen is then dialyzed against 0.005M acetic acid and freeze dried. If mature bovine hide is the source of the corium, the insoluble collagen produced is typically type I.

Soluble type IV collagen is extracted from the mouse EHS sarcoma tumor after washing the tumor in cold distilled water 3 times by spin filtration at 10,000×g for 30 minutes. The pellet (0.500 gr) is homogenized in 0.5 liters of 0.5M acetic acid adjusted to pH 2.5 with HCl and 0.5 gr of pepsin is added. The homogenate is allowed to mix at 4° C. for 24 to 48 hours, filtered through cheese cloth, spun at 10,000×g for 30 minutes. The pellet is re-suspended in 0.5M NaCl containing 50 mM Tris, NaCl is added until a final concentration of 4.5M is obtained, centrifuged at 10,000×g for 30 minutes and the pellet is dialyzed against 0.1M acetic acid 3 times and freeze dried.

EXAMPLE 2

Preparation of Bovine Serum Fibronectin

Freshly drawn bovine blood (80 ml) is collected in a polypropylene tube containing 20 ml. of 5% trisodium citrate and 0.1 mM phenylmethylsulfonyl fluoride. The blood is centrifuged at 300×g for 10 minutes and the plasma is then separated from the cell layer and further centrifuged at 30,000×g at a temperature of 15° C. for 30 minutes. To the plasma is then added an additional 1 mM of phenylmethylsulfonyl fluoride and then it is poured through a gelatin-sepharose column. The column is washed with a phosphate buffer solution (0.182M phosphate and 0.145M NaCl), 2 column volumes of 1M NaCl in a phosphate buffer, 2 column volumes of phosphate buffer solution, 2 column volumes of 4M urea in a phosphate buffer. The optical density of column fractions is monitored at a wavelength of 280 nm with the bulk of the fibronectin normally present in the fractions containing 4M urea. Fibronectin containing fractions having optical densities greater than 0.1 are dialyzed against 0.180M phosphate buffer containing 0.145M Nacl (pH 7.2). The sample is then dialyzed against 0.05M Tris—HCl containing 4.5M urea (pH 7.2) and applied to a DEAE (diethylaminoethyl cellulose) ion exchange column at room temperature. The column is eluted with a 0 to 0.3M NaCl linear gradient in a 0.05M Tris—HCl buffer solution (pH 7.2) containing 4.5M urea. The eluted fibronectin is dialyzed against 0.180M phosphate containing 0.145M NaCl and 1.0M urea and frozen at −20° C.

EXAMPLE 3

Preparation of Laminin

Laminin is prepared for lathrytic EHS tumors grown in C57/6J mice. The tumors are dissected and homogenized in 3.4M NaCl containing 50 mM Tris—HCl adjusted to pH 7.4 and protease inhibitors. The homogenate is centrifuged at 16,000×g for 60 minutes the pellet is collected and resuspeneded in 3.4M NaCl. Following centrifugation at 16,000×g for 60 minutes a second time, the homogenate is resuspended in 0.5M NaCl containing 50 mM Tris—HCl pH 7.4 and protease inhibitors stirred for 18-24 hours at 4° C. followed by centrifugation at 16,000×g for 60 min. The supernatant is brought to 3.5M by addition of solid NaCl, stirred overnight at 4° C. and the precipitate is collected by centrifugation. Laminin is further purified by redissolving in 0.5M NaCl containing 50 mM Tris—HCl pH 7.4 followed by centrifugation at 10,000×g for 60 minutes the supernatant is dialyzed against 2M urea containing 2.5 NaCl and 50 mM Tris—HCl pH 8.6 and chromatographed over a 2.5×2.5 cm. column containing DEAE cellulose equilibrated with the same buffer at 4° C. The unbound fraction is dialyzed against 2M urea containing 50 mM Tris—HCl pH 8.6 and rechromatographed on the DEAE column equilibrated with the same buffer. The unbound fraction is concentrated by vacuum dialysis and chromatographed on Sephacryl S-300 equilibrated with 1.0M CaCl$_2$, 50 mM Tris—HCl pH at 7.5 at 22° C. the void volume is collected and dialyzed against 0.4M NaCl, 50 mM Tris—HCl pH 7.4 and stored at 4° C. Laminin is resolubilized in 0.1M ammonium hydroxide pH 11.0 and then the pH is adjusted to 7.2.

EXAMPLE 4

Preparation of Collagen-Based Sponges and Sheets

Soluble or insoluble collagen (1.2 gr.) is added to 120 ml. of a dilute HCl solution of pH 3.0 and the mixture is ground in a Waring Blender at low speed for 1 minute and thereafter at high speed for 1 minute. The solution or dispersion is then poured into a vacuum flask and deaerated at a vacuum of 100 millitorr for 10 minutes. Collagen dispersions and solutions to be converted into sponges are cooled to 0° C. and frozen at −100° C. before freeze drying at −65° C. under a vacuum of less than 10 millitorr. Collagen dispersion or solutions to be processed into sheets were placed in a sterile bond and allowed to air dry for 24 to 48 hours at 22° C.

EXAMPLE 5

Preparation of Succinylated, Succinimidyl Ester Crosslinked Intermediate Collagen-Based Matrix Nine grams of succinic anhydride are dissolved in 80 ml. of distilled water and mixed for 30 minutes at 37° C. After the succinic anhydride is in solution, the pH is adjusted to 7.2 and the volume brought to 100 ml. This solution is placed in a Waring Blender and 1.0 gr. of collagen is added, ground for 2 minutes, allowed to stand at 22° C. for 1 hour, placed on Whatman #4 filter paper to remove unreacted succinic anhydride and then washed with 100 ml. of distilled water.

The residue is placed in a solution of 20 ml. of phosphate buffer (0.182M phosphate and 0.145M NaCl) and 2 gr. of N-hydroxysuccinimide and 2 gr. of cyanamide are added. The solution pH is then adjusted to 7.2. The residue is allowed to react for 3 hours at room temperature and then washed with distilled water in a Buchner funnel under a vacuum of 14 in. of Hg. Sheets and sponges of succinylated, succinimidyl ester crosslinked intermediate collagen-based matrices are produced in accordance with the processes described in Example 4.

EXAMPLE 6

Preparation of Collagen-Based Matrix Containing Fibronectin

To 1.2 gr. soluble or insoluble collagen in 120 ml. of HCl pH 3.0 is added to 0.12 gr. of fibronectin in (2.5 mg. fibronectin/ml) 0.1M urea containing 0.182M phosphate and 0.145M NaCl and the mixture is dispersed in a Waring Blender for 2 minutes. Sheets and sponges are prepared in accordance with the processes described in Example 4.

EXAMPLE 7

Sponges and Sheets Formed by Coating Type I Collagen With Laminin, Fibronectin, and Type IV Collagen Collagen sheets and sponges formed according to Examples 4 and 6 are swollen in a 0.1 ammonium acetate pH 7.2 containing 1 to 5% laminin, fibronectin or type IV collagen. The swollen sponge or sheet is then frozen and freeze dried at −65° C. and in a vacuum less than 50 millitorr.

EXAMPLE 8

Preparation of Collagen-Based Matrix Containing Hyaluronate and Proteogycans

To 1.2 gr. of soluble and insoluble collagen in HCl pH 3.0 as added to 0.12 gr. of a complex of hyaluronate and proteoglycans (Sigma Chemical Company Grade III-P) in a HCl pH 2.0 to a final volume of 120 ml. The mixture is dispersed in a Waring Blender and either freeze dried or air dried in accordance with the processes of Example 4.

EXAMPLE 9

Preparation of Collagen-Based Matrix Containing Type IV Collagen

To 1.2 gr. of soluble or insoluble collagen type I in HCl pH 2.0 is added to 0.012 gr. of type IV collagen in a 0.1M ammonium acetate pH 7.2 to a final volume of 120 ml. The mixture is dispersed in a Waring Blender for 2 minutes and formed into sheets or sponges in accordance with the processes of Example 4.

EXAMPLE 10

Cyanamide Crosslinking of Collagen-Based Matrix

The product of Examples 4 and 6 to 9 are crosslinked by immersion in an aqueous solution containing 1% by weight of cyanamide at pH 5.5 for a period of 24 hours at 22° C. After removal, the sponges and sheets are exhaustively washed in several changes of water over 24 hours, frozen and freeze dried at −65° C. in a vacuum of less than 50 millitorrs.

EXAMPLE 11

Crosslinking of Collagen-Based Matrix By Severe Dehydration

The products of Examples 4 and 6 to 10 are placed in a vacuum oven at room temperature and exposed to a vacuum of less than 50 millitorr. After one hour the samples are heated to 110° C. and remain at this temperature for 72 hours at which time the temperature is lowered to 40° C. The samples are then removed from the vacuum oven and stored −20° C.

EXAMPLE 12

Crosslinking of Collagen-Based Matrix Using Succinimidyl Active Ester

Two grams of succinimidyl active ester crosslinked collagen prepared according to Example 5 is placed in a Waring Blender containing 400 ml. of HCl pH 2.0 and dispersed for two minutes. This mixture is deaerated by placing in a vacuum of 300 millitorr and is then placed at room temperature in a 100% relative humidity environment for 24 hours. The material is then cooled to 0° C., frozen and freeze dried at −65° C. using a vacuum of less than 50 millitorr or air dried to make sponges or sheets, respectively.

EXAMPLE 13

Preparation of Collagen-Based Matrix Containing Protease Inhibitors

Sponges and sheets prepared according to Examples 4 to 9 are placed in 20 ml. of HCl at pH 2.0 containing 25% cysteine or 0.1% (W/V)α-2macroglobulin. The mixture is frozen and freeze dried at −65° C. at a vacuum of less than 50 millitorr or air dried at room temperature.

EXAMPLE 14

In Vitro Enzymatic Degradation

One $cm.^2$ of each of the products of the above Examples is placed in 2.0 ml of 10 mM Tris—HCl pH 7.4 containing 25 mM calcium chloride and 100 units of type IV collagenase from Clostridium histolyticum (Sigma Chemical Co.) is added per mg of sample. The samples are placed in a 37° C. environment and the intactness of each sample is visually checked every 10 minutes. The time is recorded when each sample has visibly degraded into pieces smaller than about 0.5 μm. The results are presented in Table I.

TABLE I

| | Physicochemical Properties of Collagen-Based Carriers | | | | | |
|---|---|---|---|---|---|---|
| Carrier Composition | Crosslinking Treatment | Physical Form | r | C.R.T.(min) | $\epsilon_f$ | HSM g mm |
| Type I Collagen | air dried | Sheet | 22.2 | 72 | 0.37 | 508 |
| Type I Collagen | SD(1) | Sheet | 7.00 | 123 | 0.25 | 850 |
| Type I Collagen | SD(2) | Sheet | 4.11 | 213 | 0.19 | 1058 |
| Type I Collagen | SD(3) | Sheet | 4.20 | 380 | 0.22 | 1468 |
| Type I Collagen | SD(5) | Sheet | 3.13 | 460 | 0.22 | 1048 |
| Type I Collagen | C(1) | Sheet | 5.88 | 105 | 0.42 | 662 |
| Type I Collagen | C(2) | Sheet | 4.48 | 123 | 0.24 | 869 |
| Type I Collagen | C(3) | Sheet | 4.69 | 185 | 0.30 | 990 |
| Type I Collagen | C(4) | Sheet | 4.29 | 237 | 0.35 | 855 |
| Type I Collagen | C(1) + SD(1) | Sheet | 2.75 | 720 | 0.15 | 1186 |
| Type I Collagen | C(1) + SD(2) | Sheet | 2.16 | 960 | 0.16 | 1441 |
| Type I Collagen | C(1) + SD(3) | Sheet | 2.62 | 1440 | 0.12 | 1872 |
| Type I Collagen | SD(3) + C(1) | Sheet | 2.75 | 960 | 0.14 | 1959 |
| Type I Collagen | SD(3) + C(2) | Sheet | 3.03 | 960 | 0.16 | 1833 |
| Type I Collagen | SD(3) + C(3) | Sheet | 3.06 | 960 | 0.11 | 1637 |
| Type I Collagen + 3% HA/PG Complex | air dried | Sheet | 23.3 | 68 | 0.34 | 615 |
| Type I Collagen + 3% HA/PG Complex | SD(3) + C(1) | Sheet | 2.31 | 1440 | 0.15 | 2275 |
| Type I Collagen + 3% HA/PG Complex | C(1) − SD(3) | Sheet | 2.56 | 1440 | 0.13 | 3434 |
| Type I Collagen | P | Sheet | 2.47 | 1515 | | |
| Type I Collagen | P + SD(3) | Sheet | 1.72 | 3180 | | |

Abbreviations:
r = swelling ratio
C.R.T. = collagenase resistance time
SD = severe dehydration at 110° C.
( ) = duration of crosslinking in days
C = 1% cyanamide immersion at 22° C.
HA/PG hyaluronate-proteoglycan complex (Sigma Chemical Co.)
$\epsilon_f$ = strain at failure
HSM = high strain modulus
P = crosslinked using succinyl ester method

EXAMPLE 15

In Vitro Determination of Swelling Ratio

The swelling ratio of denatured collagen is inversely related to the degree of crosslinking. The products of the above Examples were boiled for 2 minutes in distilled water and then blotted between two napkins. A 1 kg. weight was placed on top of the napkins containing the materials for 20 seconds. The wet sample weight was recorded and the sample was then dried at 110° C. for 3 hours. After drying the weight was again recorded and the swelling ratio (r) was calculated from the following relationship:

$$r = 1/V_f$$

layer and a 1 cm.×1 cm. piece of the implant was placed in this space. The edges of the skin were fastened together over the implant using wound clips.

Animals were sacrified on the 6th, 9th and 12th post implantation day and the tissue containing the carrier was placed in Carson's fixative and processed for histological studies. The results are presented in the following Table II.

TABLE II

In Vivo Biocompatibility of Collagen-Based Carrier Sponges Implanted Subcutaneously

| Carrier Composition | Crosslinking Treatment | Duration (days) of Implantation | Comments |
| --- | --- | --- | --- |
| Type I Collagen | None | 6 | No observable inflammatory response, no ingrowth implant intact |
| Type I Collagen | None | 9 | No observable inflammatory response, no ingrowth implant intact |
| Type I Collagen | None | 12 | No observable inflammatory response, no ingrowth implant intact |
| Type I Collagen | SD(3) | 6 | No observable inflammatory response, no ingrowth, implant intact |
| Type I Collagen | C(1) + SD(3) | 6 | No observable inflammatory response, some ingrowth at edges of sponge, implant intact |
| Type I Collagen | C(1) + SD(3) | 9 | No observable inflammatory response, peripheral ingrowth, implant intact |
| Type I Collagen | P | 6 | No observable inflammatory response, no ingrowth, implant intact |
| Type I Collagen | P + SD(3) | 6 | No observable inflammatory response, good ingrowth on periphery, implant intact |

ABBREVIATIONS:
P = crosslinked using succinyl ester method
SD = severe dehydration where $$V_f = \frac{DW/P_c}{\frac{DW}{(P_c)} + \frac{(WW - DW)}{(P_{H2O})}};$$

and where DW and WW are the dry and wet weights, $P_c$ and $P_{H2O}$ are the material and water densities, respectively. The results are presented in the aforementioned Table I.

EXAMPLE 16

Mechanical Properties of Collagen-Based Matrices

Sponges and sheets prepared in accordance with the above Examples were cut into rectangular (4.0 cm × 1.0 cm) strips and immersed in phosphate buffer solution pH 7.5 for 20 minutes prior to mechanical testing. The strips were tested in uniaxial tension at 22° C. at a strain rate of 10%/minute using an Instron Model 1122 testing device. The ends of the strips were placed in pneumatic grips that were closed under a pressure of 40 psig. with a gage length of 20 mm. Stress-strain curves were obtained from which the Young's moduli at high (HSM) and low strains were calculated. The strain at which the low modulus region ended was designated $e_L$ and the strain at failure was denoted $e_f$. The strain results are presented in Table I, above.

EXAMPLE 17

Subcutaneous Biocompatibility of Collagen-Based Matrix

Sponges and sheets prepared in accordance with to the above Examples were tested for biocompatibility subcutaneously after sterilization by exposure 2.5M rads of gamma radiation. Implantation was carried out under sterile conditions using 350 gr. white female guinea pigs as test animals.

A 1 cm. cutaneous incision was made on one side of the back and the skin was separated from the fascial

EXAMPLE 18

Preparation of Diffusion Control Layer on a Matrix Layer

Using sponges and sheets prepared in accordance with to Examples 4 to 10, a 1 mm. layer of Silastic Medical Grade adhesive was applied to the surface of the matrix layer using a spatula. The diffusion control layer is cured by application of a vacuum of 100 millitorr for a period of 2 hours at 22° C. The resultant complex of the diffusion control and matrix layers was placed in contact with full thickness dermal wounds.

EXAMPLE 19

Biocompatibility of Diffusion Control and Matrix Layers on Full Thickness Dermal Wounds Sponges and sheets prepared according to Example 18 were tested after radiation sterilization as dressings on open dermal wounds on female Hartley Albino 350 gr. white guinea pigs. Each animal was separately fed and weighed for 4 days prior to testing. One day before testing, the animal was shaved using an electric clipper followed by depilatory treatment with Nair and washed. The animal was then anesthetized by exposure to ether and its back washed with providone-iodine and alcohol solutions. A 2 cm.×2 cm. piece of material composed of matrix and diffusion control layers soaked in a phosphate buffer solution (0.182M phosphate and 0.154M NaCl), was placed on a full thickness dermal wound on the same area with the matrix layer against the panniculus carnosus. The matrix and the diffusion control layers were sutured to the wound bed at the edges of the dressing using chrome tanned gut sutures. The animals was bandaged by placing sterile cotton dressing sponge over the wound dressing and then wrapped with an Elasticon elastic tape (Johnson and Johnson Products, Inc.) secured around the neck. Animals were housed three to a cage during the experiment.

The animals were monitored daily and their bandages examined for tears. Animals were sacrified at 6, 9 and 12 day post implantation and the implant and wound beds were excised, fixed and processed for histological examination. The results are presented in Table III.

TABLE III

In Vivo Biocompatibility of Silicone Coated Collagen-Based Carriers Implanted On Full Thickness Excised Dermal Wounds

| Carrier Composition | Crosslinking Treatment Method (duration in days) | Duration (days) of Implantation | Comments |
| --- | --- | --- | --- |
| Type I Collagen | SD(3) | 6 | N.I.R., I.I., fibroblast ingrowth, synthesis of granulation tissue below implant |
| Type I Collagen | SD(3) | 9 | N.I.R., I., fibroblast ingrowth, remodeling of granulation tissue within and below implant |
| Type I Collagen | SD(3) | 12 | N.I.R., I.I., extensive fibroblast ingrowth, remodeling of granulation tissue within and below implant |
| Type I Collagen | SD(3)C(1) | 6 | N.I.R., I.I., slight fibroblast ingrowth, granulation tissue formation below implant |
| Type I Collagen | SD(3)C(1) | 9 | N.I.R., I.I., slight fibroblast ingrowth, extensive remodeling of granulation tissue below implant |
| Type I Collagen | SD(3)C(1) | 12 | N.I.R., I.I., slight fibroblast ingrowth, extensive remodeling of granulation tissue below implant |
| Type I Collagen | (1)SD(3) | 6 | N.I.R., I.I., slight fibroblast ingrowth, remodeling granulation tissue below implant |
| Type I Collagen | C(1)SD(3) | 9 | N.I.R., I.I., extensive fibroblast ingrowth, granulation tissue within and below implant |
| Type I Collagen | P | 6 | N.I.R., I.I., slight fibroblast ingrowth, granulation tissue below implant |
| Type I Collagen + 1% Laminim | SD(3) | 6 | W.I.R., I.I., slight fibroblast and capillary ingrowth, granulation tissue within and below implant |
| Type I Collagen + 5% Laminin | SD(3) + C(1) | 6 | W.I.R., I.I., extensive capillary ingrowth, granulation tissue within and below implant |
| Type I Collagen + 5% HA/PG | SD(3) + C(1) | 6 | N.I.R., I.I., extensive fibroblast ingrowth, granulation tissue within and below implant |
| Type I Collagen + 5% HA/PG | SD(3) + C(1) | 9 | N.I.R., I.I., extensive fibroblast ingrowth, remodeled granulation tissue below implant |
| Type I Collagen + 5% HA/PG | SD(3) + C(1) | 12 | N.I.R., I.I., implant remodeled after extensive fibroblast ingrowth and migration of epidermis |
| Type I Collagen + 1% Fibronectin + 1% HA/PG | C(1) + SD(3) | 9 | N.I.R., I.I., complete fibroblast ingrowth into sponges remodeled granulation tissue below sponge |
| Type I Collagen + 1% Fibronectin + 1% HA/PG | C(1) + SD(3) | 12 | N.I.R., I.I., implant remodeled after extensive ingrowth and migration of epidermis |
| Type I Collagen + 1% Fibronectin | P | 6 | N.I.R., I.I., extensive fibroblast ingrowth, granulation tissue within implant |
| Type I Collagen + 1% Fibronectin | P | 9 | N.I.R., I.I., extensive fibroblast ingrowth, granulation tissue within implant |
| Type I Collagen + 1% Fibronectin | P | 12 | N.I.R., I.I., partial epidermal migration below implant |
| Type I Collagen + 1% Fibronectin | P + SD(3) | 12 | N.I.R., I.I., extensive fibroblast ingrowth and remodeling of granulation tissue |

Abbreviations
N.I.R. = no inflammatory response; I.I. = implant intact; W.I.R. = weak inflammatory response; P = crosslinked by succinyl ester formation; SD = severe dehydration
( ) = duration of crosslinking in days; C = cyanamide treatment; HA/PG = hyaluronate-proteoglycan complex Numerous modifications and variations of the present invention are possible in light of the above teachings and, therefore, within the scope of the appended claims, the inventions may be practised otherwise than as particularly described.

What is claimed:

1. The process for the preparation of a cross-linked collagen matrix which comprises two cross-linking steps of:
   (a) contacting collagen with a cross-linking agent selected from the group consisting of a carbodiimide and a combination of a bifunctional succinimidyl active ester and a carbodiimide, and
   (b) subjecting collagen to elevated temperatures under vacuum.

2. The process of claim 1 wherein step (a) is performed prior to step (b).

3. The process of claim 1 wherein step (b) is performed prior to step (a).

4. The process of claim 1 wherein the cross-linking agent in step (a) is a carbodiimide.

5. The process of claim 4 wherein the carbodiimide is selected from the group consisting of cyanamide and 1-ethyl-3-(3-dimethylaminopropyl)-carbodiimide hydrochloride.

6. The process of claim 1 wherein the cross-linking agent is a combination of carbodiimide and a bifunctional succinimidyl active ester.

7. The process of claim 6 wherein the bifunctional succinimidiyl active ester is selected from the group consisting of bifunctional N-hydroxy succinimide, 3,3-dithro(sulfo-succinimidyl)propionate and bis(sulfosuccinimidyl) suberate and the carbodiimide is selected from the group consisting of cyanamide and 1-ethyl-3-(3-dimethylaminopropyl)-carbodiimide hydrochloride.

8. The process of claim 1 wherein step (b) is carried out at a temperature of from 50° C. to 200° C. at a vacuum of 50 millitorr or less.

9. The process of claim 8 wherein the temperature is 100° C.

10. A cross-linked matrix made according to the process of claim 1.

11. A carbodiimide and dehydrothermal cross-linked biodegradable collagen matrix which promotes fibroblast ingrowth when implanted subcutaneously or placed directly on a full thickness dermal wound.

12. The cross-linked matrix of claim 11 wherein the collagen has a minimum molecular weight of at least $1.0 \times 10^6$ daltons.

13. The cross-linked matrix of claim 12 wherein the minimum molecular weight is in excess of $50 \times 10^6$ daltons.

14. The cross-linked matrix of claim 11 wherein the molecular weight of the matrix between the covalent bond cross-links is from a minimum of 1,000 daltons to a maximum of 100,000 daltons.

15. The cross-linked matrix of claim 11 in sheet form.

16. The cross-linked matrix of claim 11 having a swelling ratio of at least about 2.5.

17. The cross-linked matrix of claim 11 which further includes a diffusion layer.

18. The cross-linked matrix of claim 17 wherein the matrix combined with the diffusion layer has a tensile strength of at least 100 psi.

19. The cross-linked matrix of claim 11 which further includes a compound selected from the group consisting of hyaluronate, fibronectin, laminin, proteoglycan, epidermal growth factor, platelet derived growth factor, angiogenesis factor, antibiotic, antifungal agent, spermicidal agent, enzyme and enzyme inhibitor, wherein the compound is cross-linked within the matrix.

20. The cross-linked matrix of claim 19 in sheet form.

21. The cross-linked matrix of claim 19 having a swelling ratio of at least about 2.5.

22. The cross-linked matrix of claim 19 which further includes a diffusion layer.

23. A carbodiimide and dehydrothermal cross-linked biodegradable matrix which consists essentially of collagen and promotes fibroblast ingrowth when implanted subcutaneously or placed directly on a full thickness dermal wound.

24. The cross-linked matrix of claim 23 wherein the collagen has a minimum molecular weight of at least $1.0 \times 10^6$ daltons.

25. The cross-linked matrix of claim 23 wherein the minimum molecular weight is in excess of $50 \times 10^6$ daltons.

26. The cross-linked matrix of claim 23 wherein the molecular weight of the matrix between the covalent bond cross-links is from a minimum of 1,000 to a maximum of 100,000 daltons.

27. The cross-linked matrix of claim 23 in sheet form.

28. The cross-linked matrix of claim 23 having a swelling ratio of at least about 2.5.

29. The cross-linked matrix of claim 23 which further includes a diffusion layer.

30. The cross-linked matrix of claim 23 wherein the matrix combined with the diffusion layer has a tensile strength of at least 100 psi.

31. A carbodiimide and dehydrothermal cross-linked collagen matrix which consists essentially of collagen and a compound selected from the group consisting of hyaluronate fibronectin, laminin, proteglycan, epidermal growth factor, platelet derived growth factor, angiogenesis factor, antibiotic, antifungal agent, spermicidal agent, enzyme and enzyme inhibitor, wherein the compound is cross-linked within the matrix, which matrix promotes fibroblast ingrowth when implanted subcutaneously or placed directly on a full thickness dermal wound.

32. The cross-linked matrix of claim 32 in sheet form.

33. The cross-linked matrix of claim 32 having a swelling ratio of at least about 2.5.

34. The cross-linked matrix of claim 32 which further includes a diffusion layer.

35. The cross-linked matrix of claim 11 wherein the collagen is selected from the group consisting of Type I, Type II and Type III collagen.

36. The cross-linked matrix of claim 11 which has a collagenase resistance time to clostridium histoylicum of from about 720 to about 3180 minutes per cm$^2$ of matrix.

37. The cross-linked matrix of claim 32 which further has a high strain modulus of from about 1186 to about 3434 g/mm.

38. The process of claim 1 wherein prior to the two crossing steps, the collagen is dispersed in dilute hydrochloric acid.

* * * * *